US00PP28438P3

(12) United States Plant Patent
Thompson

(10) Patent No.: US PP28,438 P3
(45) Date of Patent: Sep. 26, 2017

(54) ***MANGIFERA* PLANT NAMED '302216THOM'**

(50) Latin Name: *Mangifera indica*
Varietal Denomination: 302216THOM

(71) Applicant: Tim Thompson, Camarillo, CA (US)

(72) Inventor: Tim Thompson, Camarillo, CA (US)

( * ) Notice: Subject to any disclaimer, the term of this patent is extended or adjusted under 35 U.S.C. 154(b) by 0 days.

(21) Appl. No.: 14/757,211

(22) Filed: Dec. 3, 2015

(65) Prior Publication Data

US 2017/0164532 P1 Jun. 8, 2017

(51) Int. Cl.
*A01H 5/08* (2006.01)

(52) U.S. Cl.
USPC ..... Plt./159

(58) Field of Classification Search
USPC ..... Plt./159
See application file for complete search history.

(56) References Cited

U.S. PATENT DOCUMENTS

PP27,080 P3 * 8/2016 Thompson ..... Plt./159

* cited by examiner

*Primary Examiner* — Susan McCormick Ewoldt
(74) *Attorney, Agent, or Firm* — Cassandra Bright

(57) ABSTRACT

A new and distinct *Mangifera* cultivar named '302216THOM' is disclosed, characterized by a unique tolerance for cold and resistance to fungal diseases. Fruit has typically bright gold skin and juicy with very little fiber. The new variety is a *Mangifera*, suitable for the production of fruit.

1 Drawing Sheet

Latin name of the genus and species: *Mangifera indica.*
Variety denomination: '302216THOM'.

BACKGROUND OF THE INVENTION

The new *Mangifera* cultivar is a product of a planned breeding program conducted by the inventor, Tim Thompson, in Camarillo, Calif. The objective of the breeding program was to produce new *Mangifera indica* varieties with greater resistance to diseases and cold temperatures. The open pollination resulting in this new variety occurred during 1996.

The seed parent is unknown, as the inventor bulk collected seed as part of an open pollination breeding program consisting of several potential seed and pollen parents, all of which are *Mangifera indica* varieties. The new variety resulted from seed planted in 1994. The inventor observed the seedlings during several seasons, and made a final selection of '302216THOM' during 2008 at a non-commercial nursery in Camarillo, Calif.

Asexual reproduction of the new cultivar was performed by grafting vegetative cuttings onto *Mangifera indica* 'Turpentine' (unpatented). This was first performed at a commercial nursery in Ventura County, Calif. in May of 2013 and has shown that the unique features of this cultivar are stable and reproduced true to type in successive generations.

SUMMARY OF THE INVENTION

The cultivar '302216THOM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of '302216THOM'. These characteristics in combination distinguish '302216THOM' as a new and distinct *Mangifera* cultivar:

1. Good adaptation to Southern California growing conditions.
2. Tolerance for cold to approximately 28° F.
3. Resistance to powdery mildew.
4. Rich gold colored skin of the fruit.
5. Heart-shaped fruit.

PARENTAL COMPARISON

As the actual parents are unidentifiable, the inventor is unable to make any comparison.

COMMERCIAL COMPARISON

Plants of the new cultivar '302216THOM' are comparable to the variety *Mangifera* 'Kent', unpatented. The two *Mangifera indica* varieties are similar in most horticultural characteristics; however, plants of the new variety '302216THOM' differ in the following characteristics:

1. Plants of the new variety can survive cold temperatures that would damage or kill similar aged plants of 'Kent'.
2. Blossoms of the new variety are much less susceptible to powdery mildew than those of 'Kent'.
3. The new variety reliably produces a fruiting crop in Southern California, whereas plants of 'Kent' are not known to reliably produce fruit under the same environmental conditions.
4. Skin color of fruit of the new variety is typically rich gold color, whereas skin color of fruit of the variety 'Kent' is normally green on most fruit.
5. When grown in shaded conditions, the fruit skin color of 'Kent' is green, whereas '302216THOM' produces a fruit with a rich gold skin color even when grown under the shaded canopy of the tree.

Plants of the new cultivar '302216THOM' are comparable to the variety *Mangifera* 'Haden', unpatented. The two *Mangifera indica* varieties are similar in most horticultural characteristics; however, plants of the new variety '302216THOM' differ in the following characteristics:

1. Plants of the new variety can survive much colder temperatures that would damage or kill similar aged plants of 'Haden'.
2. Blossoms of this variety are relatively unaffected by powdery mildew while blossoms of 'Haden' suffer fungal damage especially during our cool, damp Spring weather.
3. The new variety reliably produces a fruiting crop in Southern California, whereas plants, of 'Haden' do not reliably produce fruit under the same environmental conditions. 'Haden' is typically does well in South Florida and Mexico conditions.
4. Skin color of fruit of the new variety is typically rich gold. Skin color of fruit of 'Haden' is typically golden with a strong red blush.
5. The variety 'Haden' is known to have significant susceptibility to fungal diseases. The new variety is significantly more tolerant of fungal diseases than 'Haden'.

Plants of the new cultivar '302216THOM' are comparable to the variety *Mangifera* '301215THOM', co-pending application Ser. No. 14/757,210. The two *Mangifera indica* varieties are similar in most horticultural characteristics; however, plants of the new variety '302216THOM' produce more inflorescence per tree, on average 100 to 150 compared to 60. Additionally, '302216THOM' produces fruit with different characteristics, as follows:

1. Fruit of '302216THOM' are heart-shaped and have an average length of 15 cm and average diameter of 5 cm; fruit of this comparator are elongated oval shaped and have an average length of 16 cm and diameter of 8 cm.
2. The stalk cavity of '302216THOM' is nearly flat, stalk cavity of this comparator is slightly recessed.
3. Fruit color of '302216THOM' is Yellow 13B and 13C with mottling Orange 26B and blush colored Orange-Red N34C. This comparator has a base color of the fruit skin of Yellow-Orange 23A and 23B, blush color is near Red 42A.

Plants of the new cultivar '302216THOM' are comparable to the variety *Mangifera* '201230THOM', U.S. Plant Pat. No. 27,080. The two *Mangifera indica* varieties are similar in most horticultural characteristics; however, plants of the new variety '302216THOM' produce fruit with different characteristics, as follows:

1. Fruit of '302216THOM' is heart-shaped, shape of this comparator is elongated.
2. '302216THOM' produces more fruit per plant, typically than this comparator
3. Fruit color of '302216THOM' is Yellow 13B and 13C with mottling Orange 26B and blush colored Orange-Red N34C. Fruit of this comparator are 80 to 90% red, RHS 53C and 53D, with a minor secondary color near Orange-Red 33B.

BRIEF DESCRIPTION OF THE PHOTOGRAPH

The accompanying photograph in:

The FIGURE illustrates in full color a typical fruit of '302216THOM'.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe '302216THOM' plants grown outdoors in Camarillo, Calif.

During the Summer months of June, July and August, the average daily high temperature is approximately 85° F. During Spring and Fall months, the daily high temperature averages about 70° F. During the Winter months of December, January, February and the first half of March the average high temperature is about 60° F. During rainy or stormy weather the daily high is about 50° F.

During the Summer months of June, July and August, the average night time temperature is about 60° F. During the Spring and Fall months, the average night time low is about 50° F. During the Winter months of December, January, February and the first half of March, the night time temperature lows range between 35° F. to 40° F. After a Winter storm moves through the area, the night time low temperature has been recorded at between 26° F. to 30° F. at the growing location during the past 30 years.

The long term precipitation records have averaged 49 cm per year in the growing area. During most of the year, the area has bright, sunny weather with brief periods during the Spring and Fall months of foggy weather. The soil is a sandy loam with good drainage. Fertilizer is a minimal, low rate, balanced organic mix. No pesticides or fungicides have been used. Measurements and numerical values represent averages of typical plant types.

Botanical classification: *Mangifera indica* '302216THOM'.

PLANT

Age of plant described: Approximately 20 years.

Vigor: This mango variety exhibits good vigor with strong support branches and supports a good mango crop.

Approximate growth rate: 90 to 120 cm of new growth per year, depending on the Summer growing season's weather.

Quantity of growth flushes per year: 90 to 120 cm good growth flushes per year depending on the year's weather.

Mean length of new shoot growth: The growth flushes vary in length in association with the weather. Spring flush shoots will be about 30 to 35 cm in length. During the warm Summer months the new growth flushes will be from 4×61 cm in length.

Height and spread: 20 years old tree is approximately 5 meters tall and to 4 meters wide.

Trunk circumference: Approximately 24 cm at the base.

Trunk color: Near RHS Greyed-Green 198 C and 198A.

Trunk texture: Rough at the base, with bark ridged approximately 2 cm deep. Gradually becoming mainly smooth at upper trunk. Upper trunk with minor vertical ridges.

Branches:

*Branch diameter at the base.*—Approximately 10 to 20 cm.

*Branch length.*—Approximately 100 to 200 cm.

*Branch texture.*—Primary branches and scaffold branches mainly smooth.

*Branch color.*—Near RHS Grey 201A, 201B and 201C.

*Lenticels.*—Not observed.

FOLIAGE

Leaf:
*Arrangement*.—Alternate.
*Quantity per branch*.—Typically 20 to 30.
*Average leaf length*.—Average range 15-20 cm.
*Average leaf width*.—Average 5 cm.
*Shape*.—Oblanceolate.
*Leaf aspect*.—Slight downward curve. Strong undulation occurring at mid point, and/or apex.
*Base*.—Cuneate.
*Margin*.—Entire.
*Leaf internode length*.—Approximately 2 cm to 2.5 cm.
*Texture of top surface*.—Glabrous.
*Texture of bottom surface*.—Glabrous.
*Appearance of top surface*.—Matte.
*Appearance of bottom surface*.—Matte.
*Color*.—Young foliage upper side: Near R.H.S. Green 137C. Young foliage under side: Near R.H.S. Yellow-Green 146C. Mature foliage upper side: Near R.H.S. Green 137A. Mature foliage under side: Near R.H.S. Yellow-Green 146D.

Venation:
*Type*.—Pinnate.
*Venation coloration upper side*.—Near R.H.S. Yellow-Green N144D.
*Venation coloration under side*.—Near R.H.S. Yellow-Green N144B.

Petiole:
*Average length*.—Approximately 6 cm for mature foliage.
*Diameter*.—Approximately 0.6 cm.
*Color*.—Near RHS Yellow-Green 144B.

FLOWER

Inflorescence type and habit: Typical mango panicle/bunch.
*Number of fruit per inflorescence*.—Some inflorescences don't set fruit. Those that do have varying numbers of fruit from 1 to 5.
*Inflorescence length*.—20 to 30 cm.
*Inflorescence diameter at the widest point*.—15 to 20 cm.
*Inflorescence rachis color*.—Near RHS Greyed-Yellow 160B.
*Mean number of inflorescences per tree*.—100 to 150.
*Mean number of flowers per inflorescence*.—From five hundred to one thousand individual blossoms per inflorescence.
*Date of first full blooms*.—Late March to early April.

Individual flowers:
General: Individual blossoms are minute.
*Diameter of open flowers*.—When fully open, approximately 7.5 mm.
*Percent hermaphrodite flowers per inflorescence*.—Approximately 40%.
*Percent male flowers per inflorescence*.—Approximately 60%.
*Floral fertility*.—Normal, the subject tree is self-fertile.
*Petals*.—Number of petals per flower: 5. Petal size: Length: 0.1 mm. Diameter: 0.02 mm. Petal texture: Slightly pubescent. Petal shape: Ovate. Petal color: Upper surface: Near RHS Yellow 13D. Lower surface: Near RHS Yellow 13D.
*Sepals*.—Number of sepals per flower: 5. Sepal size: 0.1 mm Length: 0.05 mm. Sepal texture: Densely pubescent. Sepal shape: Ovate.

Rachis:
*Length*.—Average 15 cm.
*Diameter*.—Average 0.6 cm.
*Color*.—Near RHS Yellow-Green 144B.
*Strength*.—Very strong.

REPRODUCTIVE ORGANS

Stamens: Shaped like small filaments.
*Stamen number in hermaphrodite flowers*.—5.
*Filament length*.—0.05 mm.
*Filament color*.—Near RHS Yellow-White 158C.
*Anther length*.—0.05 mm.
*Anther shape*.—Ovate.
*Anther color*.—Near RHS Yellow 10D.
*Pollen color*.—Near RHS Yellow 10A.
*Pollen production*.—Moderate.

Pistils:
*Pistil number*.—1 per flower.
*Pistil shape*.—Elliptic.
*Length*.—0.2 mm.
*Ovary number*.—Single.
*Diameter of ovary*.—0.05 mm.
*Ovary color*.—Near RHS Yellow 10D.

FRUIT

Harvest time: Fruit mature in late October through late November.
General fruit characteristics: Mature fruit is round in cross section and rich gold in color.
Fruit yield: Approximately 100 fruit on a 20 year old tree, in a non-commercial setting.
Shipping and keeping characteristics of fruit: Excellent shelf life of two to three weeks if cold storage of 50° F. is used.

Mature fruit:
*Length*.—15 cm.
*Width*.—5 cm.
*Shape*.—Somewhat heart shaped.
*Cross-sectional shape*.—Round.
*Average weight*.—14 to 18 ounces.
*Stalk cavity*.—Nearly flat.
*Skin texture of mature fruit*.—Smooth and glossy.
*Main color*.—Near R.H.S. Yellow 13B and 13C, mottling near Orange 26B, Blush near Orange-Red N34C, with dots near N34A., both colors present.
*Percentage of blush covering of fruit*.—10% on upper surface where touched by sunlight.
*Skin thickness*.—Approximately 1 mm.
*Adherence of flesh to skin*.—Skin adheres strongly to flesh.
*Lenticel spotting*.—Infrequent. Approximately 1 mm diameter, colored near Orange-Red 30D.
*Fruit flesh texture*.—Soft, juicy with very little fiber.
*Fruit flesh color*.—Near R.H.S. Orange 25A.

Seed and endocarp:
*Endocarp surface*.—Rough texture, somewhat fibrous.
*Endocarp surface color*.—Near RHS Yellow-Orange 20C.
*Endocarp plus seed dimensions*.—Endocarp: 8 cm by 4 cm, seed: 5 cm by 2.5 cm.
*Mean weight*.—2 ounces.
*Mean length*.—9 cm×4 cm.

*Seed color*.—Near RHS Yellow 10C.

*Seed size*.—5 cm×2.5 cm.

OTHER CHARACTERISTICS

Disease resistance: This mango variety has shown very good resistance to fungal diseases. No other disease problems have been observed to affect this variety.

Temperature tolerance: This variety has been unaffected by Winter low temperatures of 28° F. to 30° F. in the growing area. This variety has also survived temperatures recorded at 26° F. for up to eight hours with some frost damage to foliage and small branches.

What is claimed is:

1. A new and distinct cultivar of *Mangifera* plant named '302216THOM' as herein illustrated and described.

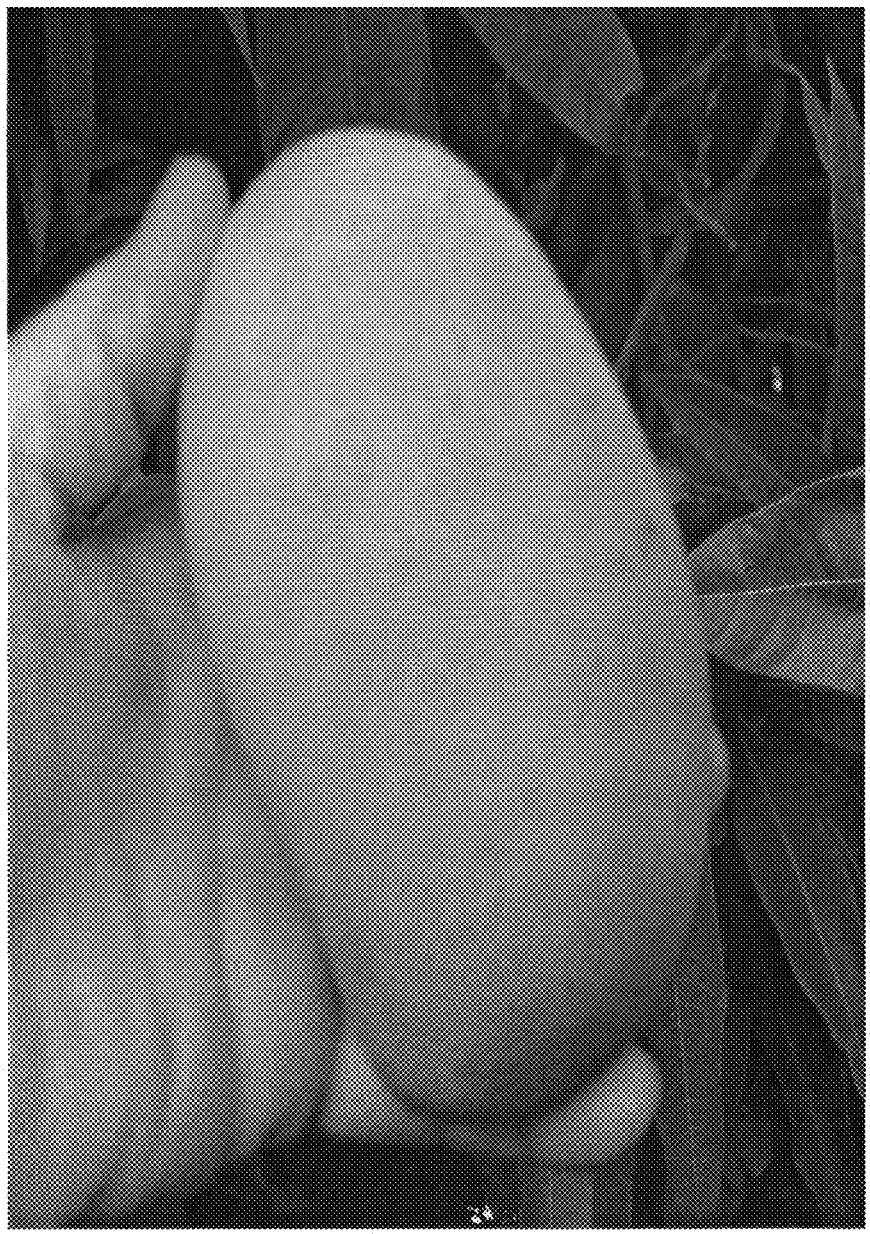

* * * * *